(12) United States Patent
Claude et al.

(10) Patent No.: US 10,153,145 B2
(45) Date of Patent: *Dec. 11, 2018

(54) METHOD OF MASS SPECTROMETRY AND A MASS SPECTROMETER

(71) Applicant: Micromass UK Limited, Wilmslow (GB)

(72) Inventors: Emmanuelle Claude, Cheshire (FR); Mark Williams Towers, Cheshire (GB); Kieran Neeson, Manchester (GB); Richard Denny, Staffordshire (GB); Jeffrey M. Brown, Cheshire (GB); Paul R. Murray, Manchester (GB); Mark McDowall, Manchester (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,800

(22) Filed: Apr. 3, 2017

(65) Prior Publication Data
US 2017/0207072 A1    Jul. 20, 2017

Related U.S. Application Data

(63) Continuation of application No. 14/551,397, filed on Nov. 24, 2014, now Pat. No. 9,613,785, which is a
(Continued)

(30) Foreign Application Priority Data

Mar. 27, 2012 (GB) .................................. 1205399.7
May 21, 2012 (GB) .................................. 1208913.2

(51) Int. Cl.
    *H01J 49/00*    (2006.01)
    *H01J 49/26*    (2006.01)
    (Continued)

(52) U.S. Cl.
    CPC ........ *H01J 49/0031* (2013.01); *G01N 27/622* (2013.01); *H01J 49/004* (2013.01);
    (Continued)

(58) Field of Classification Search
    CPC .... H01J 49/004; H01J 49/0045; H01J 49/005; H01J 49/0031; H01J 49/0036; G01N 27/622
    See application file for complete search history.

(56) References Cited

U.S. PATENT DOCUMENTS 6,872,575 B2 *   3/2005  Regnier ............. G01N 33/6803
                                                    436/149
6,982,414 B2 *   1/2006  Bateman ............. H01J 49/0031
                                                    250/282
(Continued)

*Primary Examiner* — Wyatt Stoffa

(57) ABSTRACT

The present invention relates to a method of mass spectrometry, an apparatus adapted to perform the method and a mass spectrometer. More particularly, but not exclusively, the present invention relates to a method of mass spectrometry comprising the step of associating parent and fragmentation ions from a sample by measuring the parent and fragmentation ions from two or more different areas of the sample and identifying changes in the number of parent ions between the areas in the sample, and corresponding changes in the number of fragmentation ions between the two areas.

10 Claims, 10 Drawing Sheets

Related U.S. Application Data continuation of application No. 13/851,731, filed on Mar. 27, 2013, now Pat. No. 9,048,072.

(51) Int. Cl.
  *G01N 27/62* (2006.01)
  *H01J 49/40* (2006.01)
  *H01J 49/44* (2006.01)

(52) U.S. Cl.
  CPC ........ *H01J 49/005* (2013.01); *H01J 49/0027* (2013.01); *H01J 49/0036* (2013.01); *H01J 49/26* (2013.01); *H01J 49/40* (2013.01); *H01J 49/446* (2013.01); *H01J 2237/05* (2013.01)

(56) References Cited

U.S. PATENT DOCUMENTS

| | | | | |
|---|---|---|---|---|
| 7,388,197 B2* | 6/2008 | McLean | ............... | B82Y 30/00 250/281 |
| 7,901,943 B2* | 3/2011 | Regnier | ............... | C07K 1/13 436/86 |
| 7,928,363 B2* | 4/2011 | Bateman | ............... | H01J 49/0045 250/281 |
| 2001/0052569 A1* | 12/2001 | Bateman | ............... | H01J 49/0045 250/288 |
| 2004/0041091 A1* | 3/2004 | Bateman | ............... | H01J 49/0031 250/282 |
| 2009/0148952 A1* | 6/2009 | Regnier | ............... | C07K 1/13 436/86 |
| 2010/0108878 A1* | 5/2010 | Bateman | ............... | G01N 27/622 250/283 |
| 2011/0121172 A1* | 5/2011 | Savitski | ............... | H01J 49/0045 250/282 |
| 2012/0241602 A1* | 9/2012 | Goshawk | ............... | H01J 49/0027 250/282 |
| 2013/0228678 A1* | 9/2013 | Savitski | ............... | H01J 49/0045 250/282 |
| 2014/0042314 A1* | 2/2014 | Brown | ............... | H01J 49/0072 250/282 |
| 2014/0117231 A1* | 5/2014 | Owen | ............... | H01J 37/28 250/307 |
| 2014/0158884 A1* | 6/2014 | Paluszynski | ............... | H01J 37/222 250/307 |
| 2014/0183357 A1* | 7/2014 | Smith | ............... | G01N 23/2252 250/307 |
| 2015/0136968 A1* | 5/2015 | Tate | ............... | H01J 49/0031 250/282 |
| 2015/0144778 A1* | 5/2015 | Bonner | ............... | H01J 49/0031 250/282 |

* cited by examiner

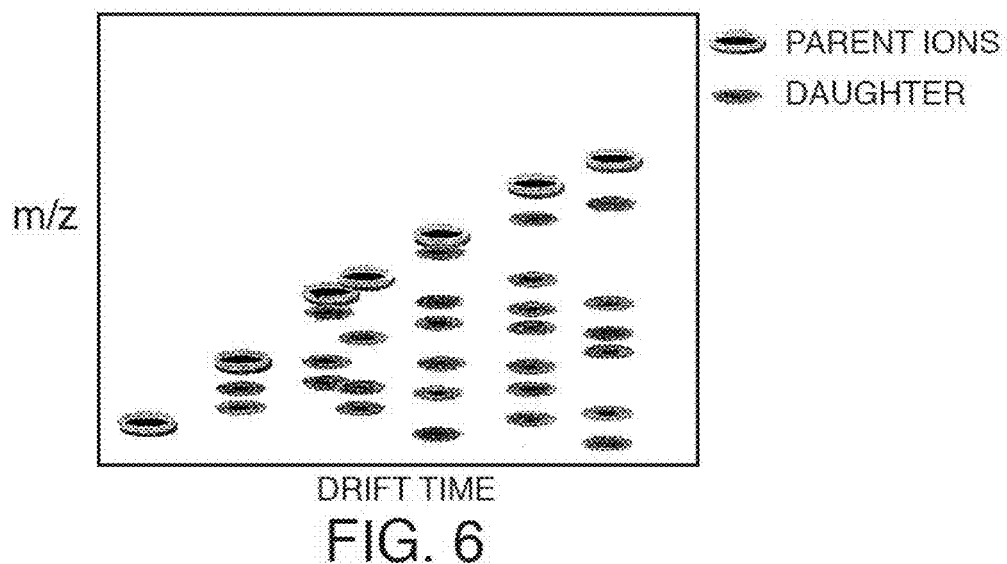
FIG. 6
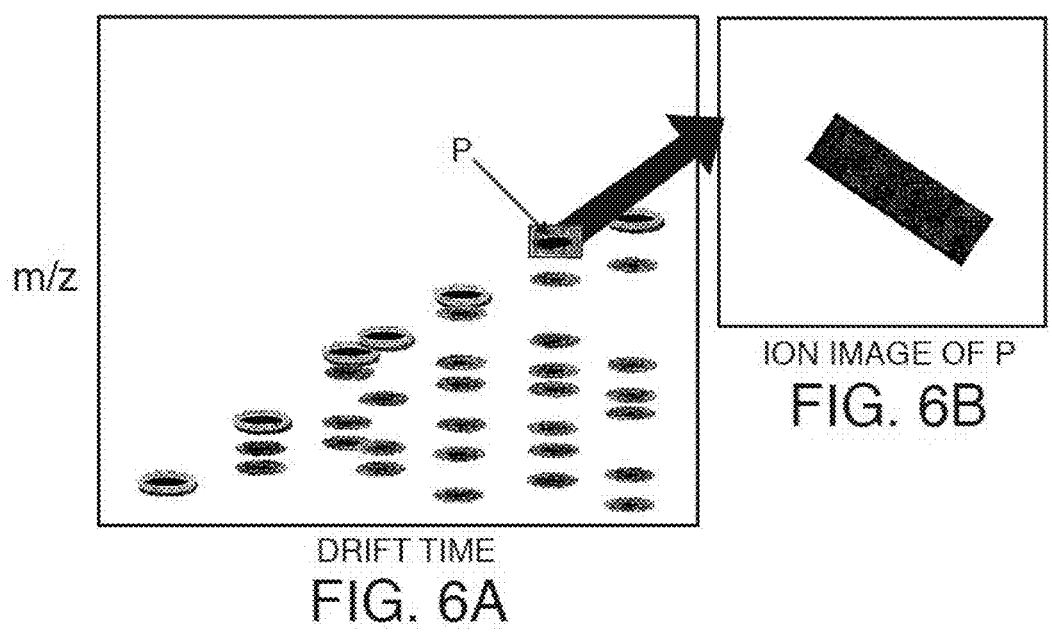
FIG. 6A
FIG. 6B

DRIFT TIME

ION IMAGE OF F1, F3, F4 AND F7

ION IMAGE OF F2, AND F6

ION IMAGE OF F5

METHOD OF MASS SPECTROMETRY AND A MASS SPECTROMETER

CROSS REFERENCE TO RELATED APPLICATIONS

This application claims priority from and the benefit of United Kingdom Patent Application No. 1205399.7, filed on Mar. 27, 2012, and United Kingdom Patent Application No. 1208913.2, filed on May 21, 2012. The entire contents of these applications are incorporated herein by reference.

BACKGROUND

The present invention relates to a method of mass spectrometry, an apparatus adapted to perform the method and a mass spectrometer. More particularly, but not exclusively, the present invention relates to a method of mass spectrometry comprising the step of associating parent (i.e. precursor) and fragmentation (i.e. daughter) ions from a sample by measuring the parent and fragmentation ions from two or more different areas of the sample and identifying changes in the number of parent ions between the areas in the sample, and corresponding changes in the number of fragmentation ions between the two areas.

It is often desirable to analyse the different areas of a biological sample to identify the substituents of the sample in the different areas. In order to perform this method, a user may perform an imaging mass spectrometry method. In such a method, the user can irradiate spots within the sample to produce ions, which reflect the constituents of the sample at the spatial position where the irradiation occurred.

Often, particularly where lipids are present in the sample, it can be difficult to identify what many of the constituents within the sample may be. In order to determine the constituents, further information relating to the structure of the constituents may be desirable. It may therefore be desirable to perform an MS/MS experiment, to give further structural information relating to the sample.

It is known to perform MS/MS on selected parent ions, and to investigate the fragments that are associated with those parents in order to identify the species that is produced. However, this approach requires parent ion selection, and results in limited information being available during the analysis, and limiting the number of components that can be identified.

Similarly, it is known to acquire a full parent ion spectrum, and a fragment ion spectrum without any mass selection. However, in this instance, it is not possible to identify which fragments result from which parent ions, meaning that identification of components within the sample is extremely difficult.

The present invention seeks to overcome the problems of the prior art.

SUMMARY OF THE INVENTION

Accordingly in a first aspect the present invention provides a method of mass spectrometry comprising the steps of:
  providing a sample;
  performing a method of association of parent analyte ions from a first area of the sample with fragmented ions from the first area of the sample comprising the steps of:
    exciting a first spot in the first area on the surface of the sample to produce a first set of parent analyte ions;
    determining the mass to charge ratio of at least some of the ions from the first set of parent analyte ions as a function of ion mobility of the ions;
    exciting a second spot in the first area on the surface to produce a second set of parent analyte ions;
    determining the ion mobility of at least some of the ions of the second set of parent analyte ions;
    fragmenting at least a portion of the second set of parent analyte ions to produce a set of fragment ions;
    determining the mass to charge ratio of at least some of the ions from the set of fragment ions as a function of the ion mobility of the ions from the second set of parent analyte ions;
    associating the set of fragment ions with the first set of parent analyte ions by comparison of the ion mobility of the ions from the first set of parent analyte ions with the ion mobility of the ions from the second set of parent analyte ions associated with the fragment ions.
  performing the method of association for at least a second area of the sample;
  assigning at least one ion from the set of fragment ions to an ion in the first set of parent analyte ions by identifying changes between the quantity of a parent analyte ion in the first area and at least the second area and corresponding changes in the quantity of at least one fragment ion in the first area and at least the second area.

The method according to the invention has the advantage that it results in the user being able to determine which fragment ions result from which parent ions and furthermore, no mass selection is required when performing the experiment.

Optionally, the change in the quantity of a parent analyte ion in the first area and at least the second area and corresponding changes in the quantity of at least one fragment ion in the first area and at least the second area are proportional to each other.

Preferably the step of determining the mass to charge ratio of at least some of the ions from the first set of parent analyte ions as a function of ion mobility of the ions comprises the steps of:
  separating the ions in an ion mobility separator; and
  determining the mass to charge ratio of at least some of the separated ions.

Optionally, the ion mobility separator separates ions into bunches, the ions in each bunch having substantially equal mobility.

Preferably, the determination of the mass to charge ratio is performed by time of flight mass spectrometry.

Optionally the step of determining the ion mobility of at least some of the ions from the second set of parent analyte ions comprises providing the ions to an ion mobility separator.

Preferably the step of determining the mass to charge ratio of at least some of the ions from the set of fragment ions as a function of the ion mobility of the ions of the second set of parent analyte ions is performed by time of flight mass spectrometry.

The first and second spots can be the same spot.
Alternatively, the second spot is proximate to the first spot
Preferably the first and second spots are excited by irradiating the spots with a laser.
Optionally a matrix is provided to the sample surface prior to exciting the spots.
Preferably, the step of:

associating the set of fragment ions with the first set of parent analyte ions by comparison of the ion mobility of the ions from the first set of parent analyte ions with the ion mobility of the ions from the second set of parent analyte ions associated with the fragment ions, is performed before the step of:

assigning at least one ion from the set of fragment ions to an ion in the first set of parent analyte ions by identifying changes between the quantity of a parent analyte ion in the first area and at least the second area and corresponding changes in the quantity of at least one fragment ion in the first area and at least the second area.

Alternatively, the step of:

assigning at least one ion from the set of fragment ions to an ion in the first set of parent analyte ions by identifying changes between the quantity of a parent analyte ion in the first area and at least the second area and corresponding changes in the quantity of at least one fragment ion in the first area and at least the second area, is performed before the step of:

associating the set of fragment ions with the first set of parent analyte ions by comparison of the ion mobility of the ions from the first set of parent analyte ions with the ion mobility of the ions from the second set of parent analyte ions associated with the fragment ions.

The method may further comprise identifying unseparated isomers from the ion mobility separator by identifying parent analyte ions and unassociated fragment ions and reviewing combined intensities of two or more unassociated fragment ions with the parent analyte ions.

Preferably, the steps of:

exciting a first spot in the first area on the surface of the sample to produce a first set of parent analyte ions; and determining the mass to charge ratio of at least some of the ions of the first set of parent analyte ions as a function of ion mobility of the ions;

are carried out after the steps of:

exciting a second spot in the first area on the surface to produce a second set of parent analyte ions;

determining the ion mobility of at least some of the ions from the second set of parent analyte ions;

fragmenting at least a portion of the second set of parent analyte ions to produce a set of fragment ions; and determining the mass to charge ratio of at least some of the ions from the set of fragmented ions as a function of the ion mobility of the ions from the second set of parent analyte ions;

Preferably, the invention further comprises the step of correlating at least two related parent analyte ions to one another by:

identifying changes between the respective quantities of two parent analyte ions in the first area and the respective quantities of two parent analyte ions in the second area.

Conveniently, the step of identifying changes in the respective quantities of parent and/or fragment ions between the first and at least second areas comprises:

producing a spectrum for the set of parent/fragment ions from the first area;

producing a spectrum for the set of parent/fragment ions for at least the second area;

conducting image analysis on the respective spectra to identify common patterns.

In a further aspect of the invention there is provided a method of mass spectrometry comprising the steps of providing a sample;

performing a method of association of parent analyte ions from a first area of the sample with fragment ions from the first area of the sample comprising the steps of:

exciting a first spot in the first area on the surface to produce a first set of parent analyte ions;

determining the ion mobility of at least some of the ions of the first set of parent analyte ions;

fragmenting at least a portion of the first set of parent analyte ions to produce a set of fragment ions;

determining the mass to charge ratio of at least some of the ions of the set of fragment ions as a function of the ion mobility of the ions from the first set of parent analyte ions;

exciting a second spot in the first area on the surface of the sample to produce a second set of parent analyte ions;

determining the mass to charge ratio of at least some of the ions from the second set of parent analyte ions as a function of ion mobility of the ions;

associating the set of fragment ions with the second set of parent analyte ions by comparison of the ion mobility of the ions from the second set of parent analyte ions with the ion mobility of the ions from the first set of parent analyte ions associated with the fragment ions.

performing the method of association for at least a second area of the sample;

assigning at least one ion from the set of fragment ions to an ion in the second set of parent analyte ions by identifying changes between the quantity of a parent analyte ion in the first area and at least the second area and corresponding changes in the quantity of at least one fragment ion in the first area and at least the second area.

In a further aspect of the invention there is provided a method of mass spectrometry comprising the steps of:

providing a sample;

performing a method of association of parent analyte ions from a first area of the sample with fragment ions from the first area of the sample comprising the steps of:

exciting a spot in the first area on the surface of the sample to produce a set of parent analyte ions;

determining the ion mobility of at least some of the ions from the set of parent analyte ions;

fragmenting a portion of the set of parent analyte ions to produce a set of fragment ions and a set of, unfragmented, parent analyte ions;

determining the mass to charge ratio of at least some of the ions from the set of parent analyte ions as a function of ion mobility of the ions;

determining the mass to charge ratio of at least some of the ions from the set of fragment ions as a function of the ion mobility of the ions from the set of parent analyte ions; and associating the set of fragment ions with the set of parent analyte ions;

performing the method of association for at least a second area of the sample;

assigning at least one ion from the set of fragment ions to an ion in the set of parent analyte ions by identifying changes between the quantity of a parent analyte ion in the first area and at least the second area and corresponding changes in the quantity of at least one fragment ion in the first area and at least the second area.

In a further aspect of the invention there is provided a method of mass spectrometry. comprising the steps of:

providing a sample;

producing a set of fragment ions by:
  exciting a spot in a first area on the surface of the sample to produce a set of parent analyte ions;
  determining the ion mobility of at least some of the ions from the set of parent analyte ions;
  fragmenting at least a portion of the set of parent analyte ions to produce a set of fragment ions;
  determining the mass to charge ratio of at least some of the ions from the set of fragmented ions as a function of ion mobility;
performing the method of producing a set of fragmented ions for at least a second area of the sample;
performing a method of relating at least two fragment ions to one another, comprising the steps of:
  associating the set of fragment ions produced from the first area with the set of fragment ions produced from the second area, as a function of the ion mobility of the set of parent analyte ions from the first and second areas.
  identifying changes between the quantity of a fragment ions in the first area and at least the second area.

In a further aspect of the invention there is provided an apparatus adapted to perform the method of any of claims 1-20.

In a further aspect of the invention there is provided a mass spectrometer comprising:
  an excitation means for exciting a sample to produce parent analyte ions;
  an ion mobility separator adapted to receive parent analyte ions and to separate the ions according to their ion mobility;
  a collision cell adapted to receive the parent analyte ions from the ion mobility separator and to fragment at least a portion of them into fragment ions;
  a Time of Flight analyser adapted to receive the parent analyte ions and fragment ions from the collision cell and produce data relating to their time of flight through the analyser; and
  processing means adapted to associate the fragment ions with the parent analyte ions by comparison of the ion mobility of the parent analyte ions with the ion mobility of the ions of the parent ions associated with the fragment ions and further adapted to assign at least one fragment ion to a parent analyte ion by identifying changes in the quantity of a parent analyte ion in different areas of the sample and identifying corresponding changes in the quantity of at least one fragment ion in the different areas of the sample.

Optionally the excitation means is a laser.

In a further aspect of the invention there is provided a computer program element comprising computer readable code means for causing a processor to implement the method of any of claims 1-20.

Preferably the computer program element is embodied on a computer readable medium.

In a further aspect of the invention there is provided a computer readable medium having a program stored thereon, where the program is adapted to make a computer execute a procedure to implement the method of any of claims 1-20.

In a further aspect of the invention, there is provided a method of mass spectrometry comprising the steps of
  providing a sample;
  performing a method of association of parent analyte ions from a first area of the sample with fragment ions from the first area of the sample comprising the steps of:
    exciting a first spot in the first area on the surface of the sample to produce a first set of parent analyte ions;
    determining the mass to charge ratio of at least some of the ions from the first set of parent analyte ions as a function of ion mobility of the ions;
    exciting a second spot in the first area on the surface to produce a second set of parent analyte ions;
    determining the ion mobility of at least some of the ions from the second set of parent analyte ions;
    fragmenting at least a portion of the second set of parent analyte ions to produce a set of fragment ions;
    determining the mass to charge ratio of at least some of the ions from the set of fragmented ions as a function of the ion mobility of the ions of the second set of parent analyte ions;
    associating the set of fragment ions with the first set of parent analyte ions by comparison of the ion mobility of the ions from the first set of parent analyte ions with the ion mobility of the ions from the second set of parent analyte ions associated with the fragment ions;
  performing the method of association for at least a second area of the sample;
  comparing at least two ions from the set of fragment ions, and ions in the first set of parent analyte ions by identifying changes between the quantity of the at least two ions from the set of fragment ions and parent analyte ions in the area and the at least one further area and identifying any co-eluting isomeric parent analyte ions.

BRIEF DESCRIPTION OF THE DRAWINGS

The present invention will now be described by way of example only, and not in any limitative sense with reference to the accompanying drawings, as follows.

FIG. 2a shows a plot of the parent ion present in a sample at a first co-ordinate. FIG. 2b shows a plot of the fragment ions present in the sample at the first co-ordinate. FIG. 2c shows a plot of the parent ion present in a sample at a second co-ordinate. FIG. 2d shows a plot of the fragment ion present in the sample at the second co-ordinate.

FIG. 3a shows a plot of the parent ions present in a sample at a first co-ordinate. FIG. 3b shows a plot of the fragment ions present in the sample at the first co-ordinate. FIG. 3c shows a plot of the parent ions present in a sample at a second co-ordinate. FIG. 3d shows a plot of the fragment ions present in the sample at the second co-ordinate.

FIG. 6 is an example data set showing a plot of drift time and mass of both parent and fragment ions. FIG. 6a corresponds to FIG. 6, in which a particular parent ion P has been indicated. FIG. 6b is the ion image of parent ion P indicated in FIG. 6a.

DETAILED DESCRIPTION

Figure 1:
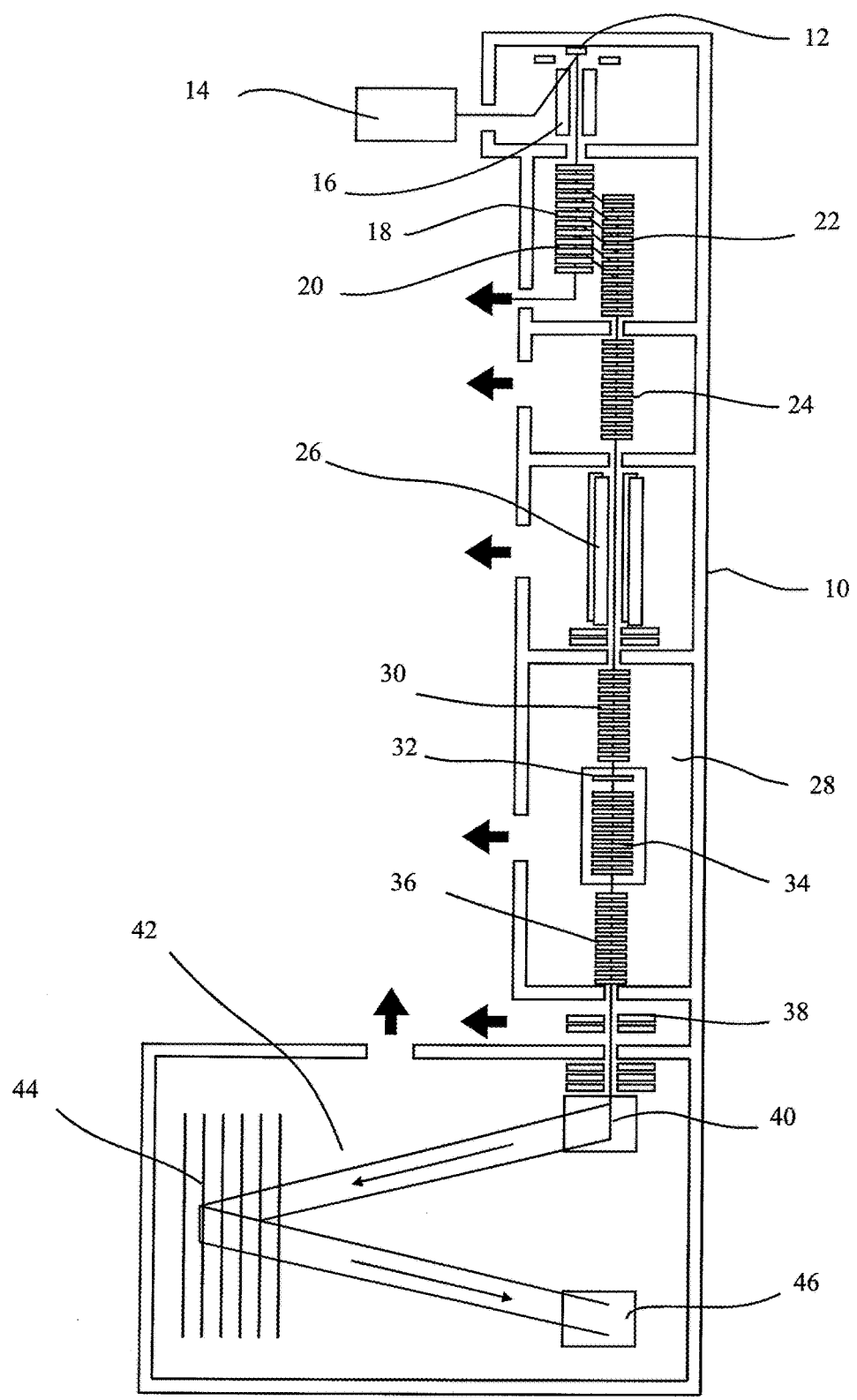
FIG. 1 is an illustration of a mass spectrometer suitable for use with the invention.

FIG. 1 illustrates a mass spectrometer 10 suitable for use with the invention. In this instrument, a sample is placed on a target 12. In a first analysis, a laser 14 is arranged to fire one or more times on a known co-ordinate on the sample. Upon firing the laser, desorption and ionisation of the sample may occur, to form sample ions. The desorbed, and ionised sample will move away from the sample plate, and the ions will flow towards a hexapole ion guide 16. The hexapole ion guide will transfer the ions from the ionisation chamber, into the stepwave ion guide 18. The stepwave ion guide will then guide the ions along the ion guide initially in a large cross section area 20 and then, focus the ions into a smaller cross section in the off axis part 22 of the guide. The ions will then be transferred into a further ion guide 24, where the ions are transmitted through to a quadrupole mass filter 26.

The quadrupole mass filter can be used in a transmission mode, so that all the ions entering, pass through the filter, and pass into the Triwave chamber 28. Once the ions are passed into the Triwave chamber 28 they are collected in bunches within the trap cell 30 within the Triwave chamber 28. A bunch of ions in the trap cell, will then be released through the helium cell 32, into the ion mobility separator 34. The ions will then temporally separate according to their ion mobility within the mobility separator, and as ions exit the separator, they are passed into a transfer cell 36, where ions of small ranges of ion mobility are collected in groups, and passed through the transfer cell, several lenses 38 and into a Tof pusher region 40. Each group of ions of small mobility ranges can then be pulsed out of the ToF pusher region into a flight tube 42, into a reflectron 44, in where they are reflected back to a detection system, where the flight times of the ions are recorded, together with the small range of mobility of the ions from that pulse.

A second analysis may then be performed along a similar basis, except, after the ions have been separated into the groups of small ranges of ion mobility in the separator 34, energy is provided to the ions within the transfer cell 36, to induce fragmentation of the ions in each group, to provide fragment ions.

These fragment ions are kept in the small groups according to the mobility of the parent ions, and are passed into the Tof pusher region 40. Similarly, each group of fragment ions from the parent ions of small mobility ranges can then be pulsed out of the ToF pusher region into a flight tube 42, into a reflectron 44, in which they are reflected back to a detection system, where the flight times of these fragment ions are recorded, together with the small range of mobility of the parent ions that produced the fragment ions within that pulse.

The information produced from each small mobility range in the first and the second analysis may be combined, to provide parent and fragment ion information for all the ions where the small range of mobility in the first and the second analysis matches.

Further analysis of more co-ordinates on the sample may then be performed to produce further parent and fragment ion information for sets of ions in each mobility range for each co-ordinate on the sample.

In one embodiment of the invention, the ions may be produced from the same coordinates on the sample for the first and the second analysis of the sample. Alternatively, the ions for the second analysis may be produced from a spot proximate to the co-ordinates from which the first ions are produced. In any event, both the first and second spots are preferably within the same area.

Figure 2A:
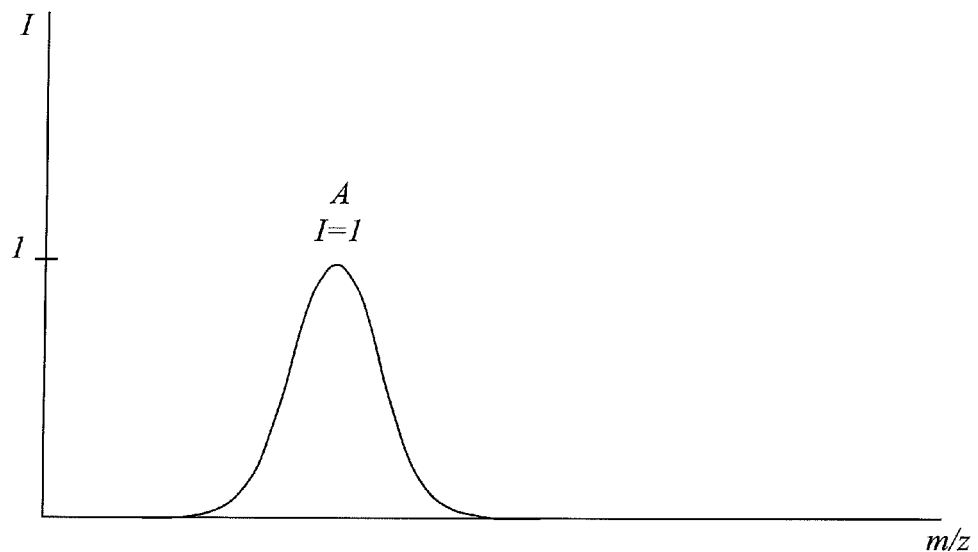
FIGS. 2a-2d show data produced from 2 different co-ordinates from an instrument according to the invention. Specifically.
Figure 2B:
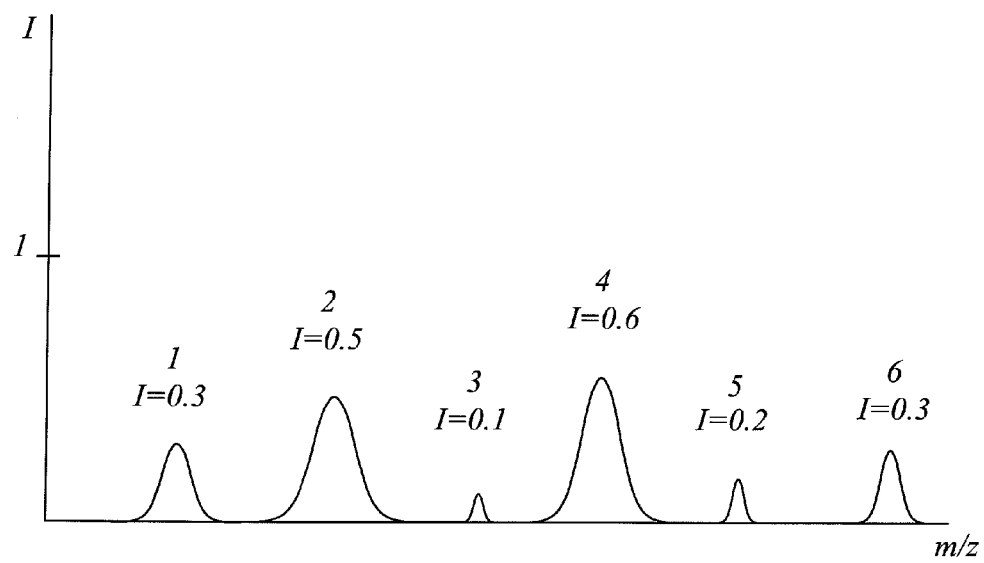
Figure 2C:
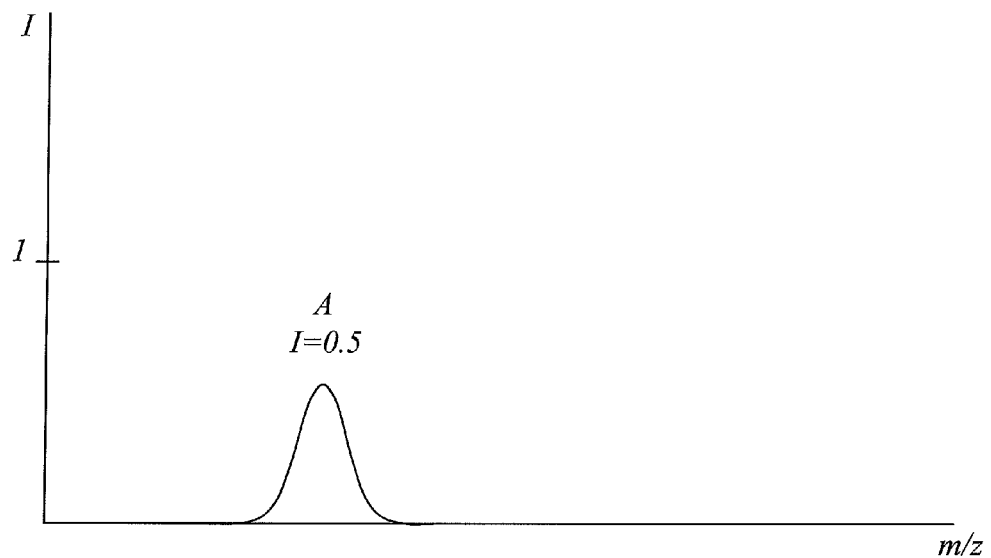
Figure 2D:
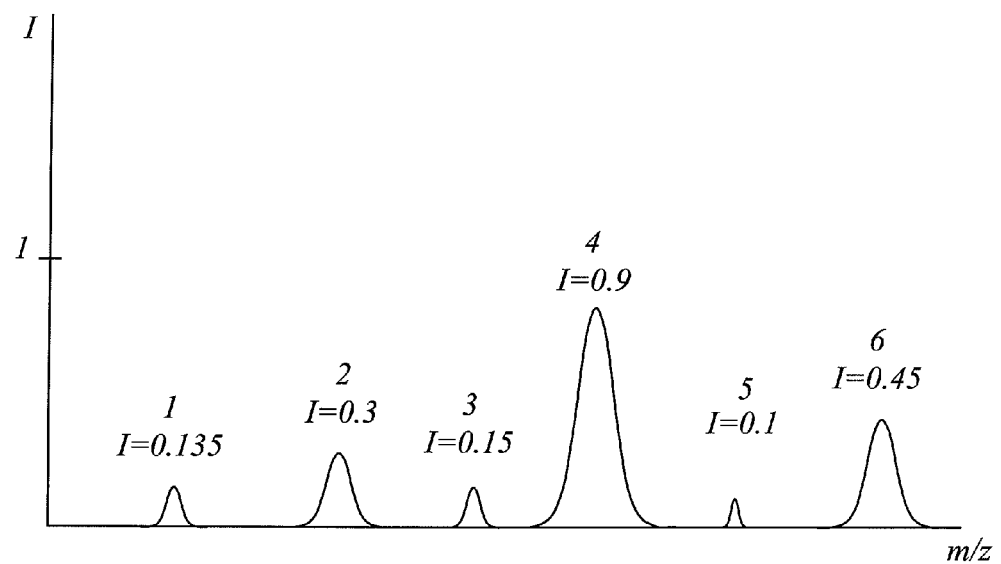

FIGS. 2a-2d shows data produced from 2 different co-ordinates from an instrument according to the invention with parent and candidate fragment information from the same range of ion mobilities at the different co-ordinates. In this data, it can be seen that the same parent ion appears in both the first data set (FIG. 2a) and the second data set (FIG. 2c). Similarly, the same candidate fragment ions appear in the two data sets (FIGS. 2b and 2d).

The intensity of the parent ion, and hence the amount of the parent ion present in the sample at that given co-ordinate, is proportional to the area of the peak. Similarly, the amount of each candidate fragment ion present in the sample at that given co-ordinate is proportional to the area of the peak for each candidate fragment ion.

In the embodiment described above, the first analysis comprises producing a first set of parent ions; and the second analysis comprises producing a second set of parent ions and then fragmenting the ions to produce a set of fragmented ions.

In another embodiment, the analyses may be performed in the opposite order. That is to say: a set of parent ions is first produced, which are fragmented to produce a set of fragmented ions. Subsequently, a further set of parent ions is produced. The ions of the further set of parent ions may then be associated with the fragmented ions, as described.

In the embodiment described above, energy is selectively provided to the transfer cell (defining the collision cell) to either fragment the parent ions or allow the parent ions to pass through unfragmented. In another embodiment, energy may always be provided to the transfer cell, and the set of parent ions is produced by bypassing the energised transfer cell.

In another embodiment, the energy provided to the transfer may be configured so as to induce fragmentation of some parent ions but not others. Accordingly, a set of ions containing both parent and fragmented ions is produced. The fragmented ions may then be associated with the parent ions. The analysis is repeated in at least one second area and the step of assigning fragmented ions to parent ions can be performed, as described above.

As the structure of the parent ion and the fragment ions may not be known, it may not be possible to determine which parent ions any particular candidate fragment ion has come from. In this example, however, by taking account of the change in the intensity of the parent ion across the two positions (co-ordinates), it may be possible to deduce which candidate fragment ions the parent ion fragments produced.

Peak A from co-ordinate 1 (FIG. 2a) has an intensity of 1. Peak A from Co-ordinate 2 (FIG. 2c), has an intensity of 0.5. Therefore, it can be deduced that the amount of the parent ion A is greater at co-ordinate 1.

Candidate fragment ions 1-6 are present in both the spectra produced from co-ordinate 1 (FIG. 2b) and 2 (FIG. 2d), and so have been identified as possible candidate fragment ions produced from parent A. However, not all these candidate fragment ions are certain to be fragments of A. In order to provide a better indication of which candidate fragment ions are produced from parent A, it may be desirable to investigate the intensities of the candidate fragments across these two co-ordinates, as it follows that the intensities of the candidate fragment ions may be proportional to the intensities of the parent ions.

As can be seen from the candidate fragment ion spectra, the intensity of candidate fragment 1 in the first co-ordinate (FIG. 2b) is 0.3, as compared to 0.135 at the second co-ordinate (FIG. 2d). The intensity of candidate fragment 2 in the first co-ordinate is 0.5, as compared to 0.3 at the second co-ordinate. The intensity of candidate fragment 3 in the first co-ordinate 0.1, as compared to 0.15 at the second co-ordinate. The intensity of candidate fragment 4 in the first co-ordinate is 0.6, as compared to 0.9 at the second co-ordinate. The intensity of candidate fragment 5 in the first co-ordinate is 0.2, as compared to 0.1 at the second co-ordinate. The intensity of candidate fragment 6 in the first co-ordinate is 0.3, as compared to 0.45 at the second co-ordinate.

Therefore, it may be deduced that the candidate fragments 1, 2 and 5 may be fragments of parent A.

Figure 3A:
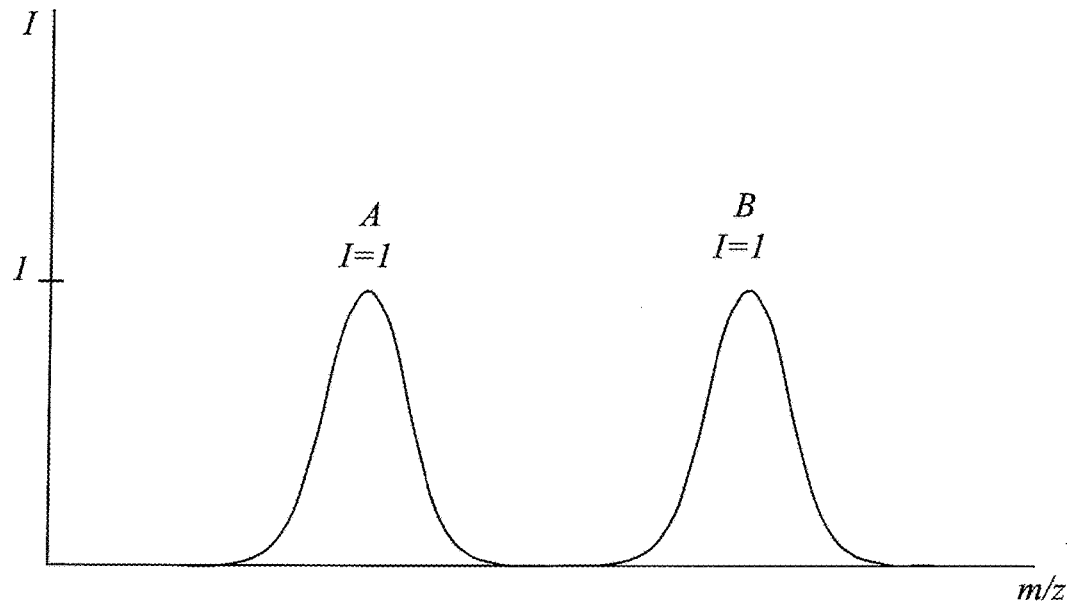
FIG. 3a-3d show data produced from 2 different co-ordinates, with two different parent ions within the same ion mobility window from an instrument according to the invention. Specifically.
Figure 3B:
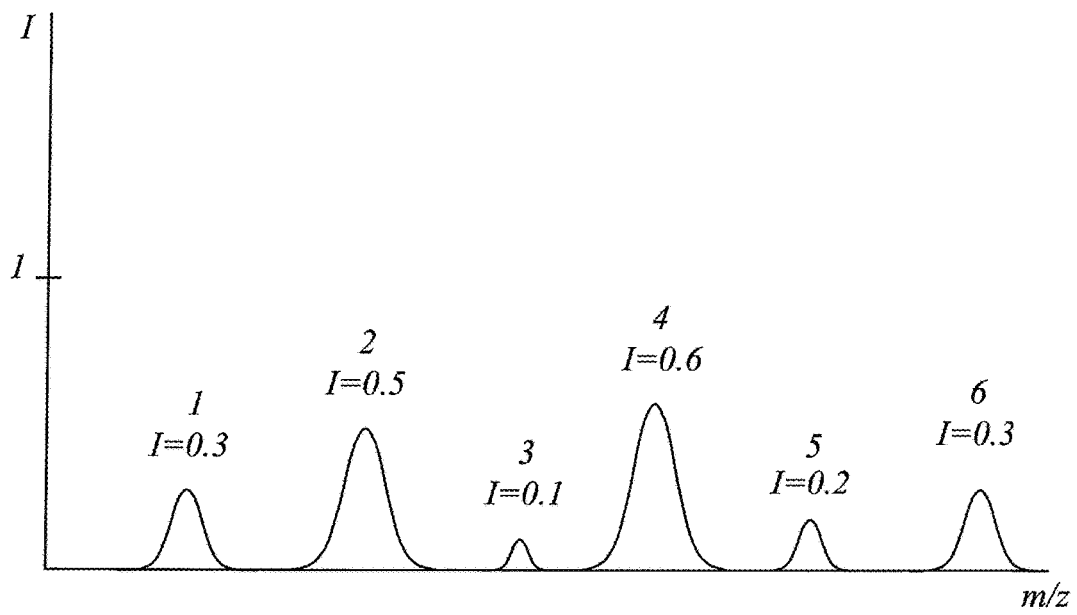
Figure 3C:
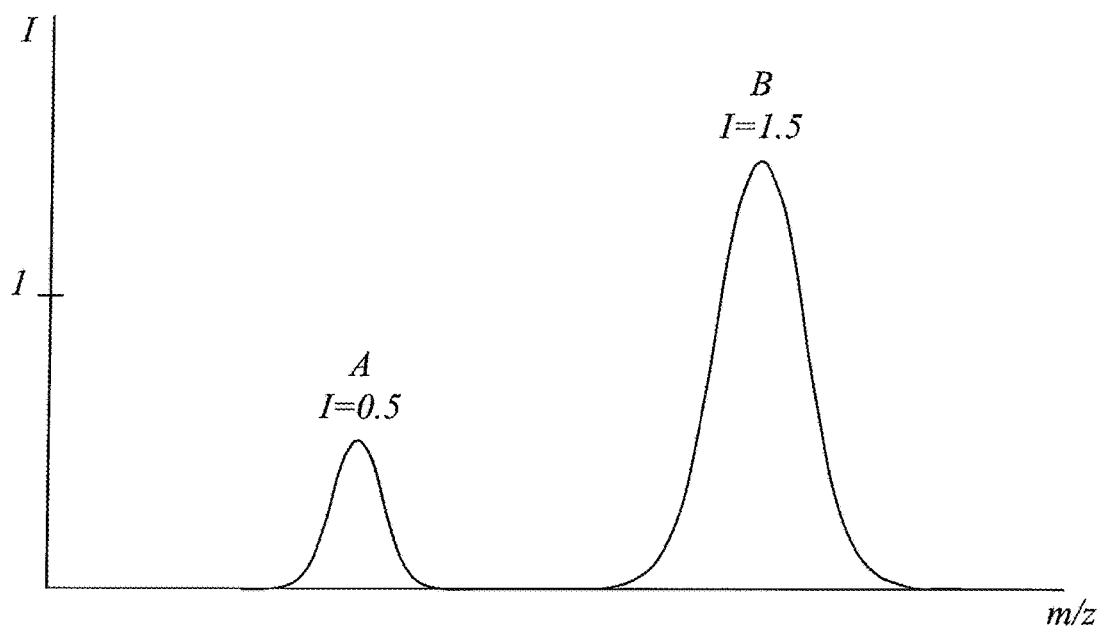

FIGS. 3a-3d show data produced from 2 different co-ordinates from an instrument according to the invention with parent and candidate fragment information from the same range of ion mobilities at the different co-ordinates. In this data, it can be seen that the same two parent ions appear in both the first data set (FIG. 3a) and the second data set (FIG. 3c). Similarly, the same candidate fragment ions appear in the two data sets.

The intensity of the parent ion, and hence the amount of the parent ion present in the sample at that given co-ordinate, is proportional to the area of the peak. Similarly, the amount of each candidate fragment ion present in the sample at that given co-ordinate is proportional to the area of the peak for each candidate fragment ion.

As the structure of the parent ions and the candidate fragment ions may not be known, it may not be possible to determine which parent ions any particular candidate fragment ion has come from. In this example, however, by taking account of the change in the intensity of the parent ions across two positions, it may be possible to deduce which candidate fragment ions any parent ion fragments produces.

Peak A from co-ordinate 1 (FIG. 3a) has an intensity of 1. Peak A from Co-ordinate 2 (FIG. 3c), has an intensity of 0.5. Therefore, it can be deduced that the amount of the parent ion A is greater at co-ordinate 1 (FIG. 3a). Peak B from co-ordinate 1 (FIG. 3a) has an intensity of 1. Peak B from Co-ordinate 2 (FIG. 3c), has an intensity of 1.5. Therefore, it can be deduced that the amount of the parent ion B is greater at co-ordinate 2 (FIG. 3c).

Candidate fragment ions 1-6 are present in both the spectra produced from co-ordinate 1 (FIG. 3b) and 2 (FIG. 3d), and so have been identified as possible candidate fragment ions produced from parent A. However, not all these candidate fragment ions are certain to be fragments of A. In order to provide a better indication of which candidate fragment ions are produced from parent A, it may be desirable to investigate the intensities of the candidate fragments across these two co-ordinates, as it follows that the intensities of the candidate fragment ions may be proportional to the intensities of the parent ions.

Figure 3D:
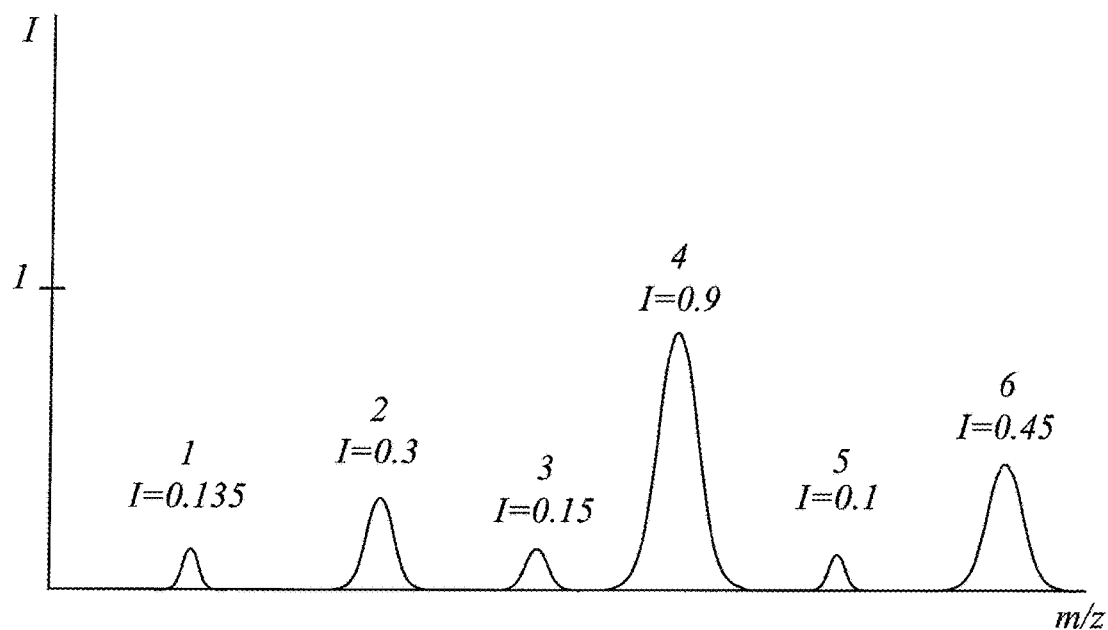

As can be seen from the candidate fragment ion spectra, the intensity of candidate fragment 1 in the first co-ordinate (FIG. 3b) is 0.3, as compared to 0.135 at the second co-ordinate (FIG. 3d). The intensity of candidate fragment 2 in the first co-ordinate is 0.5, as compared to 0.3 at the second co-ordinate. The intensity of candidate fragment 3 in the first co-ordinate is 0.1, as compared to 0.15 at the second co-ordinate. The intensity of candidate fragment 4 in the first co-ordinate is 0.6, as compared to 0.9 at the second co-ordinate. The intensity of candidate fragment 5 in the first co-ordinate is 0.2, as compared to 0.1 at the second co-ordinate. The intensity of candidate fragment 6 in the first co-ordinate is 0.3, as compared to 0.45 at the second co-ordinate.

Therefore, it may be deduced that the candidate fragments 1, 2 and 5 may be fragments of parent A. Similarly, it can also be deduced that the candidate fragments 3, 4 and 6 may be fragments of parent B.

Where Data sets are larger than a few peaks, or many co-ordinates are analyzed, there may be significantly more data to analyze. This can be done by similar means to those described for small numbers of peaks, although it would be apparent to those skilled in the art that the amounts of data would make this potentially difficult to analyze optically. Therefore, for data sets where large numbers of co-ordinates have been analyzed, it may be necessary to use an algorithm in order to fully identify the parent and fragment correlations, and subsequently assign fragmentation ions to parent ions.

The correlation may be performed using the Pearson product-moment correlation coefficient.

In this method, the degree of data correlation is expressed using the Pearson product-moment correlation coefficient. This is a measurement of the linear dependence between two variables. The result of the calculation is an r value between −1 and +1, which is a measure of the degree of correlation with negative numbers indicating a negative correlation; and positive numbers indicating a positive correlation.

| r number result | Degree of correlation |
| --- | --- |
| −1 to −0.5 | Strong negative correlation |
| −0.49 to −0.3 | Medium negative correlation |
| −0.29 to −0.1 | Small negative correlation |
| −0.09 to +0.09 | No correlation |
| +0.29 to +0.1 | Small positive correlation |
| +0.49 to +0.3 | Medium positive correlation |
| +1 to +0.5 | Strong positive correlation | the equation used for the calculation can be seen below:

$$r = \frac{\sum_{i=1}^{n}(X_i - \overline{X})(Y_i - \overline{Y})}{\sqrt{\sum_{i=1}^{n}(X_i - \overline{X})^2}\sqrt{\sum_{i=1}^{n}(Y_i - \overline{Y})^2}}$$

where $X_i$ and $Y_i$ are paired measurements for variable X and variable Y, and X is the parent ion peak and Y is the candidate fragment ion peak.

The paired measurements for two variables X and Y are compared in terms of the degree to which the measurements deviate from their mean. Strong positive correlations will be observed when the measurements for the two variables change to the same degree in the same direction (both increase or both decrease). Strong negative correlations will be observed when the measurements change to the same degree but in the opposite direction (x increases and y decreases or x decreases whilst y increases).

In this instance the variables represent ions present in the sample and the paired measurements are the intensity of these ions within the same pixel or adjacent pixel.

Other known methods of correlating the intensities of the parent and fragment ion intensities may include Spearman's rank correlation coefficient or Spearman's rho, Kendall rank correlation coefficient, Distance correlation, Brownian covariance and Brownian distance covariance. It would be apparent to one skilled in the art how to use these methods to perform the function.

Figure 4:
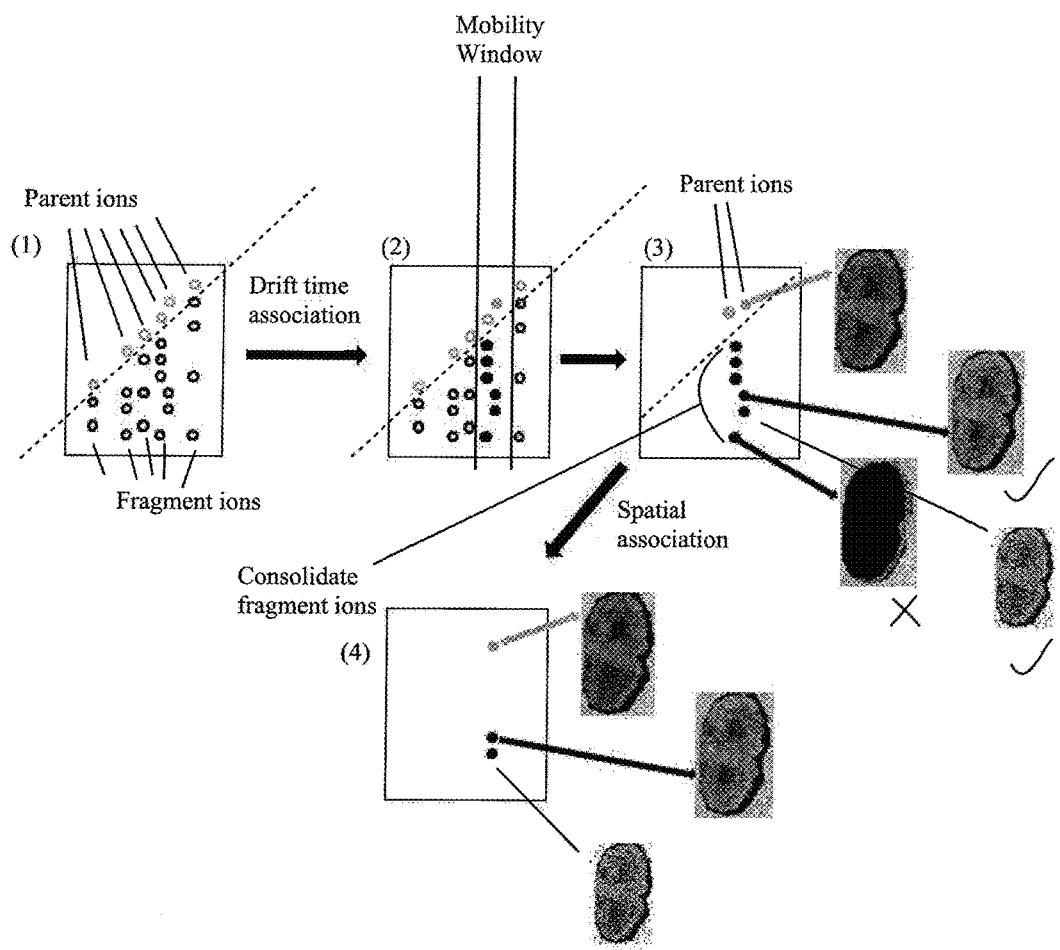
FIG. 4 is an illustration of a method according to the invention.

FIG. 4 is an illustration of a method according to the invention. In this figure, MALDI, IMS, MS and MS/MS analysis has been done on many co-ordinates upon the sample as described above. In this illustration, the drift time and mass of parent and fragment ions have been plotted at point 1 across the whole of the image. If a specific drift time window of interest is selected, then the highlighted points on 2 are present within the window. It is desirable to be able to identify which of these candidate fragments result from the parent of interest. Stage 3 shows a set of fragment ions that may relate to a selected parent ion. A further way of analysing the sample in accordance with the invention may be to use a pattern recognition program to identify the related parent and fragment ions. Fragments and parents mapped against the co-ordinates on the sample and from the same mobility range can be differentiated by reviewing the image of their intensity across the co-ordinates analysed.

As can be seen in FIG. 4, at point 4 the images for the parent and fragments are similar across the whole sample, though the intensities of the fragments may be less that those of the parent. Similar to the algorithms, this is an alternative way of performing the analysis of the sample in accordance with the invention.

It would be apparent to a person skilled in the art that any method of pattern recognition is actually a method of identifying changes between the quantity of the parent analyte ion in multiple areas in the sample and corresponding changes in the quantity of at least one fragmented ion in multiple areas in the sample. Changes in the respective quantities of parent and/or fragmented ions between the first and at least second areas can be identified by producing spectra for the parent/fragmented ions from both the first and second areas, and then conducting image analysis on the respective spectra to identify common patterns.

Figure 5:
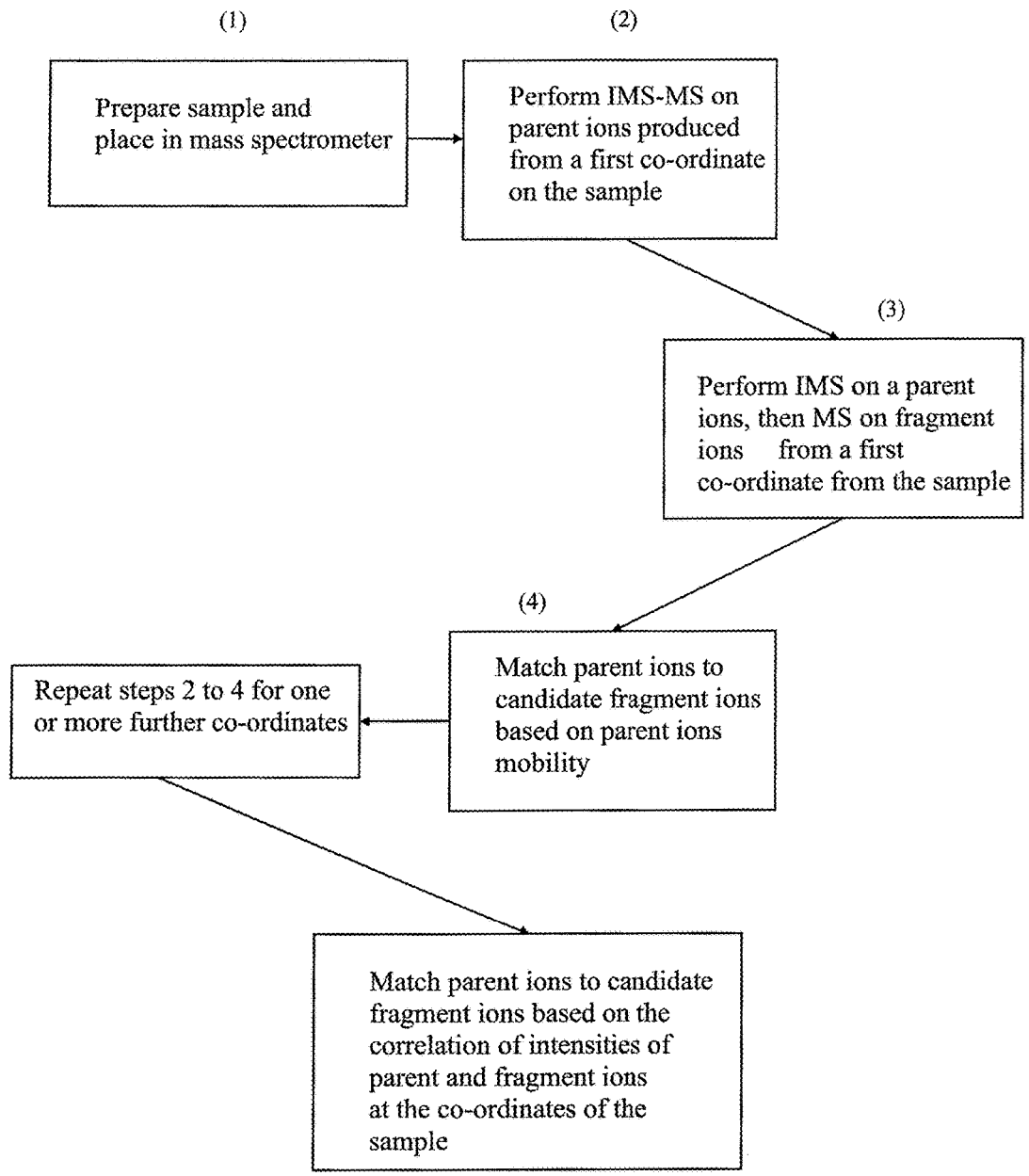
FIG. 5 is a flow chart illustrating a work flow in accordance with the invention.

FIG. 5 is a flowchart illustrating a work flow in accordance with the invention. In this figure, a workflow in accordance with the invention may be seen. A sample may be prepared by known methods 1, then parent ion IMS/MS may be performed on the analyte from a specific co-ordinate 2. After this, parent ion IMS, fragmentation, then MS on the fragment ions is performed 3. Matching the parent ions and candidate fragment ions according to the parent ions IMS drift time can be performed 4. Analysis of further co-ordinates can then be performed 5 by repeating steps 2-4. Once analysis has been finished, matching of parent ions to candidate fragment ions based on the correlation of intensities of the parent and fragment ions at the co-ordinates of the sample can be performed.

In one embodiment the Ion mobility separator may be a Travelling wave Ion Mobility Separator. Alternatively, the ion mobility separator may be a drift tube Ion Mobility Separator.

In one embodiment the method of excitation of the sample may be a laser. In other embodiments the excitation may be an ion gun, a piezoelectric device, any form of impaction, heat, a gas flow, any form of particle beam, an electron beam, an ion beam or SIMS.

The method of excitation may be in an ion source. Preferably the ion source may be DESI, LESA, DART, MALDI, LDI, IR MALDI, UV MALDI, Laserspray, AP MALDI, Intermediate pressure MALDI, Vacuum MALDI or SELDI.

In some embodiments of the invention the quadrupole may be arranged to filter ions so that ions outside a mass range of interest do not pass through the quadrupole into the Triwave.

In some embodiments of the invention the sample on the sample plate may be provided with a matrix, to assist ionisation and desorption of the sample. This Matrix may be from the group comprising Butanedioic acid, pyridine-3-carboxylic acid, 3-(3,4-Dihydroxypheny)l 2-propenoic acid, 3-(4-hydroxy-3,5-dimethoxyphenyl)prop-2-enoic acid, 1,8-dihydroxy-9,10-dihydroanthracen-9-one, 2',6'-Dihydroxyacetophenone, 2,5-Dihydroxybenzoic acid, 3-Hydroxypicolinic acid, 3-Aminoquinoline α-Cyano-4-hydroxycinnamic acid, 2',4',6'-Trihydroxyacetophenone, 4-chloro-α-Cyanocinnamic acid, 1,5-diaminonapthalene, 2-(4'-hydroxybenzeneazo) benzoic acid alpha-cyano-2,4-difluorocinnamic acid, 9-aminoacridine, 2-(2-aminoethylamino)-5-nitropyridine, para-nitroaniline or 2-mercaptobenzo-thiazole.

The Time of Flight tube may be arranged to have one reflectron within the path of ions being analysed. In other embodiments the Time of Flight tube may be arranged to have multiple reflectrons within the path of the ions being analysed.

The sample may be a biological sample, alternatively, the sample may be a polymer, a tablet, a PCB, a silicon wafer, a metal plate, petrochemical residue or a food surface.

In one embodiment the sample may be a surface of interest. This may be a tissue slice, or section from a patient of interest, a slice or section from any sample of interest listed above or a complete surface or sample of interest.

In one embodiment the sample may be the deposition of sample eluted from an LC column onto a surface. In this instance the co-ordinates on the sample surface may relate to the elution time of the analyte from the LC column. It would be apparent to the skilled person that in this instance the correlation of the intensities of the parent and fragment ions will be applied over fewer areas, which relate to elution times within a small range.

In embodiments of the invention the sample may include lipids, proteins, peptides, metabolites, sugars or any other endogenous species. In other embodiments, the sample may include plastics, paints, inks, paints and other materials and/or other surfaces.

In one embodiment of the invention, the sample plate may move, and the laser may remain stationary when changing from one co-ordinate to another. In an alternative embodiment the laser may move and the sample plate may remain stationary when changing from one co-ordinate to another. In a further alternative, the sample plate and the laser may both move when changing from one co-ordinate to another.

It would be apparent to the person skilled in the art that alternative structures of mass spectrometers may be used to perform the invention. For example, it would be apparent to the skilled person that different inlet systems could be used instead of a hexapole and a stepwave device. Similarly, it would be apparent to the skilled person that the quadrupole is not essential to perform the invention.

It would also be apparent to the skilled person that an ion trap could be used to collect bunches of ions exiting the ion mobility separator. In this instance, a collision cell may be arranged after the ion trap, to fragment the parent ions for the second analysis.

In further embodiments of the invention, correlation of the intensities of the parent and fragment ions may be performed before the IMS correlation is performed. This may be particularly useful where images of the whole of the area that has been analysed has been compared.

In further embodiments of the invention, where no, or incomplete correlation between parent and fragment ion peaks has been observed, it may be possible to identify co-eluting isomers from the Ion Mobility Spectrometer by reviewing the fragment ion intensity data for the fragments present in the mobility window, and reviewing the combined intensities of two or more fragment ions, to further review for correlations with the intensities of the parent ion.

In a situation where two isomeric parent ions have similar drift times it may not be possible to distinguish between the parent ions in the ion image. However, if the parents have different sets of daughter ions then the correlation of the daughter ion images may give clarification as to which daughter ions originate from which parent. When the parent ion and daughter ion driftscope plots are viewed they may appear similar to the FIG. 6.

Selecting one region of drift time associated with a parent ion P with a given m/z, as shown in FIG. 6a, allows an ion image to be generated for that particular parent ion as also illustrated in FIG. 6b.

Figure 7:
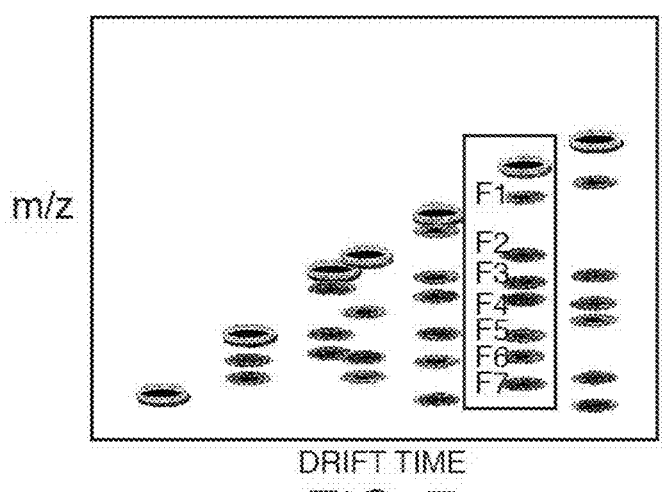
FIG. 7 is an example data set which corresponds to FIG. 6, in which a set of fragment ions F1-F7 have been indicated.

Similarly, each of the fragment ions can generate an ion image as shown in FIG. 7.

Figure 7A:
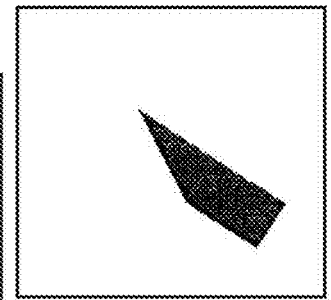
FIG. 7a is the ion image of fragment ions F1, F3, F4 and F7.
Figure 7B:
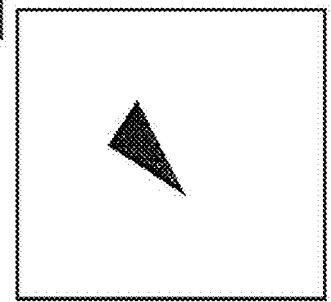
FIG. 7b is the ion image of fragment ions F2 and F6.
Figure 7C:
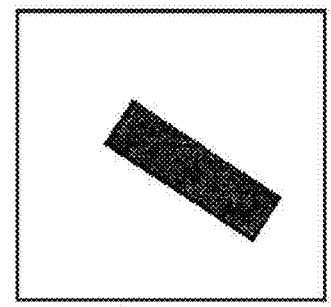
FIG. 7c is the ion image of fragment ion F5.

From this example it can be seen that only the daughter, F5, truly correlates with the spatial distribution generated by the parent ion image (as shown in FIG. 7c), whereas the others only have a partial correlation (as shown in FIGS. 7a and 7b). This suggests that the parent ion map actually consists of more than one isomeric species, co-eluting from the IMS cell. One parent ion, P1, fragments to produce daughters, F1, F3, F4, F5 and F7. Whereas, a second, isomeric parent ion P2 fragments to produce daughters, F2, F5 and F6.

In a further embodiment of the invention there may therefore be an advantage in correlating the daughter ions ion images, not only with the parent ion image, but also with other daughter ion images so that a more specific identification may be performed.

Figure 8:
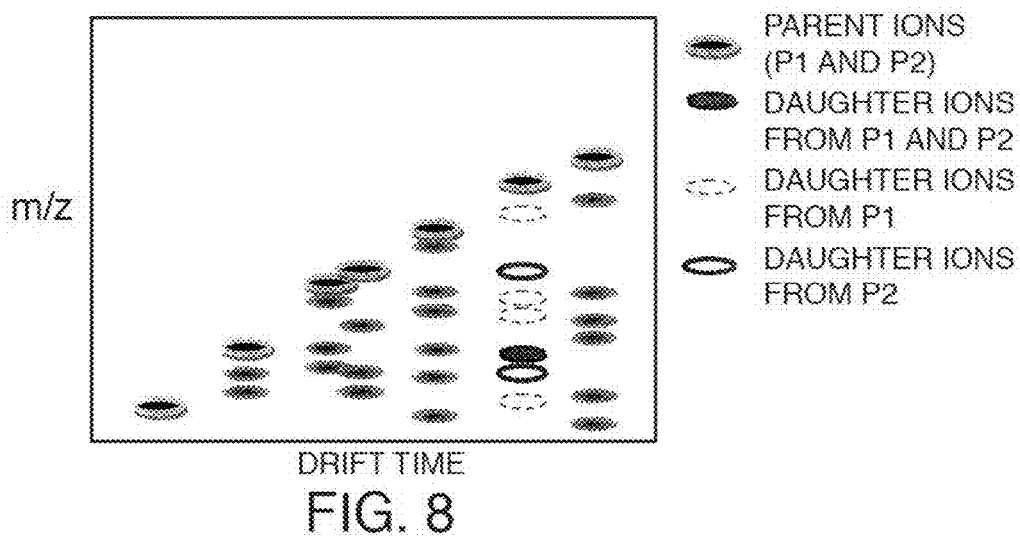
FIG. 8 is an example data set showing deduced inferences from which the daughter ions originate in accordance with one embodiment of the invention.
Figure 8A:
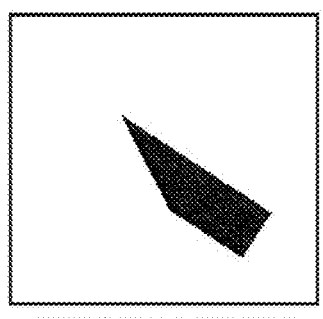
FIG. 8a is the ion image of ion P1.
Figure 8B:
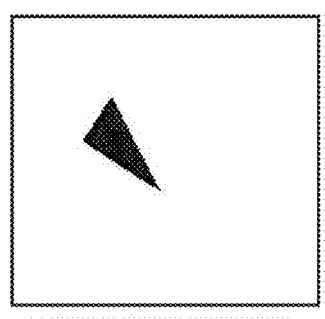
FIG. 8b is the ion image of ion P2.

The driftscope plot can hence be further identified as shown in FIG. 8, and the ion images can be refined to specify the distributions of the two (or more) parent ion species (as shown in FIGS. 8a and 8b).

In addition to assigning fragmented ions to parent analyte ions by way of drift time alignment and correlation of the ion signal distribution, using the Pearson product correlation calculation, parent analyte ions can be correlated with other parent analyte ions. This can be used to determine parent analyte ions which may have come from the same digested/in-situ pre fragmented/modified analyte or from analytes that share the same distribution pattern.

This method may not be limited to protein digestion but can also be utilised with other in-situ modifications such as deglycosylation, adduct formation etc, in which multiple parent ions may come from the same analyte.

A method embodying the present invention may comprise the step of correlating at least two related parent analyte ions to one another by:
  identifying changes between the respective quantities of two parent analyte ions in the first area and the respective quantities of two parent analyte ions in the second area.

The step of correlating two parent ion analytes preferably adopts a clustering technique. Parent ions may be clustered into groups based on their distance from each other, wherein that distance is a function of their correlation to each other based on their signal distribution. Two clustering techniques which may be utlilised are Hierarchal clustering and straight K-means/K-Medoid clustering.

In embodiments of the various clustering techniques, the following common steps may be followed:
  produce a correlation matrix whereby the correlation co-efficient of each peak is calculated against all other peaks.
  calculate the distance of each peak from each other peak based on the correlation co-efficient;
  convert the correlation table into a distance table
  define clusters of peaks based on their distance from each other.

In other embodiments, image analysis may be used. For example, a spectrum is produced for the set of parent ions from the first and at least second areas, and then the spectra are compared to one another to identify common patterns.
Hierarchal Clustering Hierarchal clustering can be performed using agglomerative "bottom-up" clustering or divisive "top-down" clustering, both of which will now be described.
Bottom Up Agglomerative Clustering For bottom up agglomerative clustering, each peak would be assigned to its own cluster containing only that single peak. Clusters can then be merged with other clusters based on their distance from each other, using predetermined distance metric and linkage criteria. Within each iteration, the two clusters which are closest together, based on the predetermined criteria, are merged into one cluster.

This process continues until a single cluster containing all the peaks is formed. The order in which the clusters were merged is used to form a hierarchal cluster tree. The lower down the tree two particular clusters are, the higher the likelihood of correlation between the peaks in those clusters.

The key considerations in ensuring the effective implementation of bottom up clustering are the distance metric and linkage criteria. The distance metric defines how the distances are calculated and the linkage criteria are used to determine how clusters are iteratively merged.

One distance metric which may be used is to adopt the correlation score as the distance. The distance between two peaks is taken to be measured by the correlation score which is converted to a positive scale. i.e. d=(1−r)/2 where r is the correlation score. d has a range of 0 to 1, wherein 0 is an exact positive correlation and 1 is an exact negative correlation.

$$\text{Distance} = \frac{(1 - \text{Correlation})}{2}$$

Other suitable distance metrics may instead convert the correlation scores to coordinates in n-dimensional space. Each peak is represented by an axis in the n-dimensional space, the axis extending from −1 to +1. For a given peak, the correlation scores between the given peak and the other peaks are converted to coordinates on that axis. For example, if there are 1000 peaks in the data set, the data would be projected on to a 1000 dimensional model. The distance between the peaks can then be calculated in relation to their distance from each other in n-dimensional space. This information is then used in the clustering step A number of algorithms can be used to calculate the distance between the peaks for clustering using this n-dimensional model. Two suitable algorithms are Euclidean and Euclidean squared distance.

Euclidean:

$$\|a-b\|_2 = \sqrt{\sum_i (a_i - b_i)^2}$$

Euclidean Squared:

$$\|a-b\|_2^2 = \sqrt{\sum_i (a_i - b_i)^2}$$

In which a is the coordinate of the first peak on axis i and b is the coordinate of the second peak on axis.

Other suitable distance metrics suitable, which would be known to the skilled person, are: Manhatten, Chebychev and correlation (Pearson or Spearman).

The linkage criteria is used to determine which clusters should be merged. Three linkage criteria which may be used are:
  Maximum or complete linkage, in which the distance between two clusters is determined to be the distance between the two peaks within the clusters (one for each cluster) which are furthest apart in terms of the calculated distance using the distance metric.
  Minimum or single linkage, in which the distance between two clusters is determined to be the distance between the two peaks within the clusters (one for each cluster) which are closest together in terms of the calculated distance using the distance metric.
  UPGMA or average/mean linkage, in which the mean value for the coordinates for the peaks within the clusters is calculated. The distance between the clusters is then calculated based on the distance between these calculated mean values, using the distance metric.

The clusters which are determined to be closest together are merged until all clusters are merged into one cluster.

Other suitable linkage types, which would be known to the skilled person, are: centroid linkage, density linkage and two stage linkage.

Top-down Divisive Clustering

For top down divisive clustering the peaks all start by being assigned to a single cluster. Subsequent splitting of the cluster may then be performed using either K-means or K-Medoid clustering, in which K=2, As with agglomerative clustering, the correlations are projected into an n-dimensional model with the correlation scores being converted to coordinates on an axis, with each peak being represented by a respective axis. The distances between points are calculated using the Euclidean distance metric, as described above.

Two peaks are chosen at random and assigned as the K-mean starting points. The distances from the respective peaks to these points are calculated, and the peaks are assigned to the cluster centre to which they are closest. The average K-mean centre for that cluster is calculated for K-means. This becomes the new cluster K-means centre. Using the K-medoid method, the peak closest to this centre is defined as the new centre. The distances from the respective peaks from these new centres is then calculated and the peaks are again assigned to the cluster centre they are closest to. The new K-mean or K-medoid centres are then calculated. This process continues until the calculated centres no longer change.

Since the starting points are randomly selected, it is possible that there may be more than one possible solution to the clustering. Optionally, the process can be repeated using different starting points. After repeating the process a number of time, the results of each iteration can be reviewed and the optimal clustering model determined.

A method of determining the optimal cluster splitting model is to calculate the sum of the distances for the peaks to their respective assigned cluster centre. The model having the lowest sum of the distances may be elected as the optimum cluster division result.

Subsequently, the data is split into two clusters and the process is repeated on the two new clusters. This process continues until all clusters contain only 1 peak.

Other suitable hierarchical methods, which would be known to the skilled person, are EML (equal-variance maximum liklihood), flexible-beta, McQuittys, Median and Wards minimum variance method.

Non Hierarchial K-mean/K-medoid Clustering

For non-Hierarchal clustering using K-mean/K-medoid clustering, the value of K is increased to the desired number of clusters. For example, K=10 would produce 10 clusters. The basic principle is the same as for hiererchial clustering. That is to say that the correlations are projected on to the n-dimensional model and random start points are generated for each K mean, i.e. 10 random start points. Peaks are then assigned to clusters based on their distance from the k mean cluster centres. The distance metric used is the Euclidian distance. The K-mean or K-medoid centre is then re calculated—as with the top down hierarchal clustering method—and the process continues until the calculated centres no longer change. This process can also be iterated as with the top down hierarchal clustering in order to try and determine the optimal split.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A method of mass spectrometry comprising the steps of:
  providing a sample;
  performing a method of analysis of parent analyte ions and fragment ions from a first area of the sample, comprising the steps of:
    exciting a first spot in the first area of the sample to produce a first set of parent analyte ions;
    determining quantities and mass to charge ratios of at least some of the ions in the first set of parent analyte ions;
  exciting a second spot in the first area of the sample to produce a second set of parent analyte ions;
    fragmenting at least a portion of the second set of parent analyte ions to produce a set of fragment ions;
    determining quantities and mass to charge ratios of at least some of the ions in the set of fragment ions from the second set of parent analyte ions;
  performing the method of analysis for at least a second area of the sample;

determining changes in the quantity of a parent ion in the first area and at least the second area and changes in the quantity of at least one fragment ion in the first area and at least the second area; and assigning at least one ion from the set of fragment ions to an ion in the first set of parent analyte ions by identifying changes between the quantity of a parent analyte ion in the first area and at least the second area and corresponding changes in the quantity of at least one fragment ion in the first area and at least the second area.

2. The method as claimed in claim 1, wherein the change in the quantity of a parent analyte ion in the first area and at least the second area is proportional to corresponding changes in the quantity of at least one fragment ion in the first area and at least the second area.

3. The method as claimed in claim 1, further comprising identifying at least one ion from the set of fragment ions for which the changes in the quantity of any parent analyte ions in the first area and at least the second area do not correspond with changes in the quantity of the at least one fragment ion in the first area and at least the second area thereby providing an indication of potential parent analyte ions which are isomers or other ions of the same mass to charge ratio.

4. The method as claimed in claim 1, wherein the first and second spots are the same spot.

5. The method as claimed in claim 1, wherein the second spot is proximate to the first spot.

6. The method as claimed in claim 1, further comprising providing a matrix to the sample surface prior to exciting the spots.

7. The method as claimed in claim 1, further comprising: determining the ion mobility of at least some of the ions of the first and second sets of parent analyte ions;

wherein the mass to charge ratio of at least some of the ions from the first and second sets of parent analyte ions is determined as a function of ion mobility of the ions; and associating the set of fragment ions with the first set of parent analyte ions by comparison of the ion mobility of the ions from the first set of parent analyte ions with the ion mobility of the ions from the second set of parent analyte ions associated with the fragment ions.

8. The method as claimed in claim 1, wherein the steps of:

exciting a first spot in the first area of the sample to produce a first set of parent analyte ions; and determining quantities and mass to charge ratios of at least some of the ions of the first set of parent analyte ions;

are carried out after the steps of:

exciting a second spot in the first area to produce a second set of parent analyte ions;

fragmenting at least a portion of the second set of parent analyte ions to produce a set of fragment ions; and determining quantities and mass to charge ratios of at least some of the ions in the set of fragmented ions from the second set of parent analyte ions.

9. The method of mass spectrometry according to claim 1, wherein the step of identifying changes in the respective quantities of parent and/or fragment ions between the first and at least second areas comprises:

producing an image of the sample, showing the relative quantities of each parent ion across the sample;

producing an image of the sample, showing the relative quantities of each fragment ions across the sample; and conducting image analysis on the respective images to identify common patterns.

10. The method of mass spectrometry according to claim 9 wherein the image analysis further comprises identifying parent images and fragment images which correspond.

\* \* \* \* \*